United States Patent [19]

Ribaldone et al.

[11] Patent Number: 4,511,718
[45] Date of Patent: Apr. 16, 1985

[54] PREPARATION OF PYRAZINE DERIVATIVES

[75] Inventors: Giuseppe Ribaldone, Gallarate; Maria G. Felicioli, Novara; Claudio Santini, Novara; Giovanni Agnes, Novara, all of Italy

[73] Assignee: Farmitalia Carlo Erba S.p.A., Milan, Italy

[21] Appl. No.: 471,691

[22] Filed: Mar. 3, 1983

[30] Foreign Application Priority Data

Mar. 8, 1982 [GB] United Kingdom ................ 8206772

[51] Int. Cl.³ .................. C07D 241/14; C07D 401/02; C07D 413/02; C07D 417/02
[52] U.S. Cl. .................................... 544/406; 544/120; 544/357
[58] Field of Search ........................................ 544/406

[56] References Cited

U.S. PATENT DOCUMENTS 2,520,088 8/1950 Jones .................................. 544/406

FOREIGN PATENT DOCUMENTS 1361967 7/1974 United Kingdom ................ 544/406

OTHER PUBLICATIONS

Sato, "J. Het. Chem.", vol. 15, (1978), p. 665.
Taylor et al., "J. Org. Chem.", vol. 46, (1981), p. 1394.

Primary Examiner—Donald G. Daus
Assistant Examiner—William A. Teoli, Jr.
Attorney, Agent, or Firm—Oblon, Fisher, Spivak, McClelland & Maier

[57] ABSTRACT

A process for the preparation of a pyrazine derivative of the formula

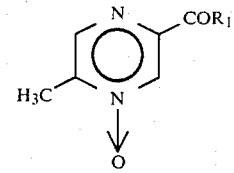

wherein $R_1$ represents hydroxy, $C_1$-$C_6$ alkoxy, or a group of the formula $NR_2R_3$ in which $R_2$ and $R_3$ are independently a hydrogen atom or $C_1$-$C_6$ alkyl or, together with the nitrogen atom to which they are linked, form a saturated ring having five or six atoms which may contain one or more additional heteroatoms; which process comprises reacting a compound of the formula:

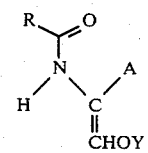

wherein R represents a hydrogen atom, $C_1$-$C_6$ alkyl, or $C_1$-$C_6$ alkoxy, Y represents a hydrogen atom or a sodium, lithium, or potassium ion, and A is a nitrile group or a substituent of the formula $COR_1$ where $R_1$ is as defined above either with pyruvic aldehyde oxime of the formula:

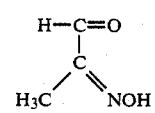

or with a pyruvic aldehyde oxime acetal derivative of the formula:

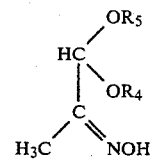

wherein $R_4$ and $R_5$ are independently a hydrogen atom or $C_1$-$C_6$ alkyl or may be linked together so that the compound of formula IV is a cyclic acetal; and, when A is a nitrile group, hydrolyzing the reaction product.

8 Claims, No Drawings

PREPARATION OF PYRAZINE DERIVATIVES

BACKGROUND OF THE INVENTION

1. Field of the Invention

The present invention relates to a method for the preparation of pyrazine derivatives of the formula

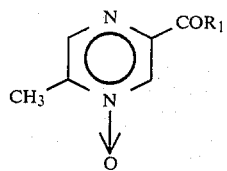

wherein $R_1$ represents a hydroxyl group, a $C_1$–$C_6$ alkoxyl group, or a group of the formula $NR_2R_3$ in which both $R_2$ and $R_3$ are independently a hydrogen atom or a $C_1$–$C_6$ alkyl group, or are linked together to form a saturated ring having five or six atoms and optionally containing other heteroatoms such as O, N, and S. Preferred ring systems so formed are piperidine, pyrrolidine, morpholine, piperazine, and thiazolidine. In particular, the method is useful for the preparation of 5-methyl-pyrazin-1-carboxylic-4-oxide acid ($R_1$=OH).

2. Description of the Prior Art

Compounds of formula I as above defined have been recognized as having hypolipoemic or hypoglycaemic activity as more clearly demonstrated in British Patent Specification No. 1,361,967.

The patent also discloses a method for preparing compounds of formula I by the oxidation of a compound of the formula:

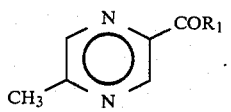

wherein $R_1$ is as previously defined, by means of hydrogen peroxide. While this previously described process may be satisfactory for producing small quantities of pyrazine derivatives, the use of a dangerous oxidizing reagent such as hydrogen peroxide is not suitable for industrial scale production. Applicants have surprisingly found a novel and certain method for preparing compounds of formula I on a large scale without use of an oxidizing reagent.

GENERAL DESCRIPTION OF THE INVENTION

Pyrazine derivatives of formula I, where $R_1$ is as defined above, can be prepared according to the instant invention by condensing a compound of the formula

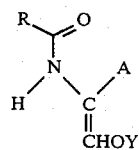

in which R represents a hydrogen atom, $C_1$–$C_6$ alkyl, or $C_1$–$C_6$ alkoxy, Y represents a hydrogen atom, a sodium ion, a potassium ion, or a lithium ion, and A is a nitrile group or a substituent of the formula $COR_1$, in which $R_1$ has the same significance as defined above, with pyruvic aldehyde oxime of the formula III

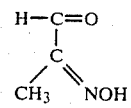

which can be used in the form of its acetal derivative IV

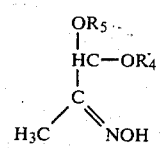

wherein $R_4$ and $R_5$ are independently a hydrogen atom or $C_1$–$C_6$ alkyl, or may be linked together to form a cyclic acetal of formula IV; and, if A is a nitrile group, hydrolyzing the reaction product. If desired, one can convert a compound of formula I so produced into another compound of formula I by a method known per se.

Acetal derivatives of formula IV may be generated in situ from the reaction between a pyruvic aldehyde dialkyl or cyclic acetal

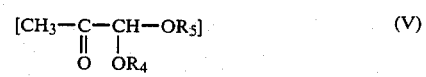

where $R_4$ and $R_5$ are as defined above, with hydroxylamine according to known methods in this field.

Compounds of formula II have been prepared according to the methods described by Ellis V. Brown, *Chemistry of Penicillin*, Princetown University Press 1949, pages 473–534, or by obvious variations of this method.

It should be noted that such compounds can be indicated not only by formula II (adopted by applicants in accordance with the convention of E. V. Brown), but also by formula VI,

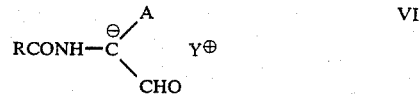

where R, A, and Y have the same significance as described above. In fact, formulae II and VI constitute limit formulae presumably present together and in equilibrium, and suitable for indicating one and the same compound.

Compounds of formulae III and IV have been prepared according to conventional methods (see, for instance, G. T. Newbold, W. Sharp, and F. S. Spring, *J. Chem. Soc.*, 1951, 2679).

PREFERRED EMBODIMENTS OF THE INVENTION

The reaction between compounds of formula II with compounds of formula III and/or IV, to which the present invention refers, is preferably carried out in the presence of organic or inorganic acids in a suitable solvent, at a temperature falling between 15° C. and the boiling point of the chosen solvent. The preferable acids are hydrochloric acid, hydrobromic acid, hydroiodic acid, sulfuric acid, nitric acid, p-toluenesulphonic acid, formic acid, phosphoric acid, methanesulphonic acid, trifluoroacetic acid, and trifluoromethanesulphonic acid. The solvent is preferably chosen from among $R_7OH$ alcohols, $R_7OR_6$ ethers,

ketones,

esters or organic acids, in which both $R_7$ and $R_6$ are independently a hydrogen atom and branched linear or cyclic chain alkyls containing 1 to 6 carbon atoms and, where both are present, can be joined together to form any of a cyclic ether, a cyclic ketone, or a lactone. Representative solvents include ethanol, isopropyl alcohol, and dioxane.

This reaction is carried out preferably using equimolecular quantities of II and III, or II and IV or II with a mixture of pyruvaldehyde V and hydroxylamine capable of forming III.

The dilution proportions between II (or III) and the solvent preferably range from 1:10 and 1:100, but even higher dilutions may be used.

When A in formula III is nitrile, the compounds of formula I can be prepared by hydrolysis of the product obtained by condensation of II with III and/or IV according to known methods.

A compound of formula I prepared in accordance with the present invention can be converted to another compound of formula I by methods known per se. For example, a compound of formula I where $R_1$ is alkoxy or a $NR_2R_3$ group can be converted into a compound of formula I where $R_1$ is hydroxy by saponification with an aqueous alkali or by hydrolysis.

The examples given below are merely indicative and in no way limit the field of the present invention.

EXAMPLE 1

Into a reactor there was placed dioxane (50 ml), methyl α-formyl-N-formyl glycinate sodium salt (II, where R=H, $R_1$=OCH$_3$, Y=Na) (2 g), methyl glyoxime-dimethyl acetal (IV, where $R_4$=$R_5$=CH$_3$) (1.6 g), and a 35% HCl solution (2 ml).

The whole mixture was stirred for 5 hours at a temperature of 45° to 50° C. maintained thermostatically.

A white solid (NaCl) was formed and was filtered off. The solvent was eliminated under vacuum and the residue was taken up and recrystallized from methanol to give 1.1 g of methyl-4-oxide 5-methyl-pyrazin-2-carboxylate.

Yield: 56%
Melting point: 146°–147° C.

EXAMPLE 2

Isopropyl alcohol (25 ml), ethyl α-formyl-N-formyl glycinate sodium salt (II, where R=H, $R_1$=OC$_2$H$_5$, Y=Na) (1 g), methylglyoxime dimethylacetal (IV, $R_4$=$R_5$=CH$_3$) (0.75 g), and a 35% HCl solution (1 ml) were placed in the reactor and the resulting mixture was stirred for 5 hours at 60° C. Thereafter, the solvent was evaporated under vacuum. Ethanol (25 ml) was added and the whole mixture was allowed to stand for 10 hours, which resulted in 0.48 g (48% yield) of ethyl-4-oxide 5-methyl-pyrazin-2-carboxylate.

EXAMPLE 3

Ethyl α-formyl-N-formyl glycinate sodium salt (II, R=H, $R_1$=OEt, Y=Na) (5 g) was introduced into a reaction flask, along with methyl glyoxime dimethyl acetal (IV, where $R_4$=$R_5$=CH$_3$) (3.7 g), isopropyl alcohol (125 ml), and conc. HCL (35%) (5 ml).

The mixture was stirred for 6 hours at 60° C. and the resulting NaCl was filtered off.

After being cooled to 0° C. and saturated with gaseous NH$_3$, the filtrate gave after 10 hours a precipitate of 1.9 g of 5-methyl-pyrazin-2-carboxamide-4-oxide which is isolated and is equivalent to a yield of 45%.

M.pt.=209°–210° C.

EXAMPLE 4

Ethyl α-formyl-N-formyl glycinate sodium salt (II, where R=H, $R_1$=OC$_2$H$_5$, Y=Na) (1 g), methylglyoxime dimethylacetal (IV, where $R_4$=$R_5$=CH$_3$) (0.75 g), and 85% HCOOH in water (25 ml) were placed in a reaction flask and the whole mixture was stirred for 5 hours at 50° C.

The formic acid and water were distilled off under vacuum. Ethanol (30 ml) containing 1% HCl was added to the residue and the mixture was then refluxed for 3 hours. There was obtained 0.33 g of ethyl-4-oxide 5-methyl-pyrazine-2-carboxylate (33% yield).

EXAMPLE 5

Ethyl α-formyl-N-formyl-glycinate sodium salt (II, R=H, $R_1$=OC$_2$H$_5$, Y=Na) (1 g), methylglyoxime dimethylacetal (IV, where $R_4$=$R_5$=CH$_3$) (0.75 g), ethyl acetate (25 ml), and conc. HCl (35%) (1 ml) were introduced into a reaction flask and the mass was stirred for 8 hours at 50°–55° C. Further treatment was carried out as described in Example 2 to give 0.45 g of ethyl-4-oxide 5-methyl-pyrazine-2-carboxylate, a yield of 45%.

EXAMPLE 6

Operating according to the method and quantities given for the first part of Example 3, and replacing the conc. HCl with para-toluenesulphonic acid (2 g), 0.37 g (37% yield) of ethyl-4-oxide 5-methyl-pyrazin-2-carboxylate was obtained.

EXAMPLE 7

Operating according to the quantities and method established in Example 5, but replacing the ethyl acetate with the same quantity (25 ml) of acetone, 0.36 g of ethyl-4-oxide 5-methyl-pyrazin-2-carboxylate was obtained (36% yield).

EXAMPLE 8

Ethyl α-formyl-N-formyl glycinate sodium salt, (II, where R=H, $R_1$=OEt, Y=Na) (1 g), pyruvic aldehyde oxime (III) (0.5 g), conc. HCl (35%) (1 ml), and isopropyl alcohol (25 ml) were introduced into the reaction flask.

The mass was kept at 60° C. for 8 hours. On operating as described in Example 5, 0.31 g of ethyl-4-oxide 5-methyl-pyrazin-2-carboxylate was obtained.

EXAMPLE 9

Pyruvaldehyde dimethylacetal (V, R$_4$=R$_5$=CH$_3$) (4.2 g) was placed in a reaction flask. Then, 2.45 g of NH$_2$OH.HCl disolved in 10 ml of H$_2$O and brought to pH 7 with Na$_2$CO$_3$, were added to the flask. This operation is carried out at 5°–10° C. Thereafter, 120 ml of 98% HCOOH and 5.6 g of ethyl α-formyl-N-formyl glycinate sodium salt (II, R=H, R$_1$=OEt, Y=Na) were added after 30 minutes. The mixture was stirred for 5 hours at 50° C. On operating as described in Example 4, 1.4 g of ethyl-4-oxide 5-methyl-pyrazin-2-carboxylate was obtained.

EXAMPLE 10

Ethyl α-formyl-N-carbethoxyglycinate sodium salt (II, where R=R$_1$=OC$_2$H$_5$, Y=Na) (1 g), methylglyoxime dimethylacetal (IV, where R$_4$=R$_5$=CH$_3$) (0.6 g), isopropyl alcohol (25 ml), and HCl (35%) (0.8 ml) were placed in a reaction flask. The mass was then refluxed for 10 hours, with stirring.

There was obtained 0.21 g of ethyl-4-oxide 5-methyl-pyrazin-2-carboxylate equivalent to a yield of 27.2%, after the usual treatment.

EXAMPLE 11

Methyl α-formyl-N-acetylglycinate sodium salt (II, where R=CH$_3$, R$_1$=OCH$_3$, Y=Na) (8 g), methylglyoxime dimethylacetal (IV, where R$_4$=R$_5$=CH$_3$), 200 ml of isopropyl alcohol, and 7.5 ml of 35% HCl are placed in the reaction flask.

The mass was stirred for 5 hours at 60° C.

There was obtained 3 g of methyl-4-oxide 5-methyl-pyrazin-2-carboxylate (40% yield) after the usual treatment.

EXAMPLE 12

The purpose of this example is to show conversion of a compound of formula I prepared in accordance with the present invention into another compound of formula I.

Ethyl-4-oxide 5-methyl-piperazine-2-carboxylate-4 (4.5 g) was added to 10% (W/V) sodium hydroxide (45 ml) and the mixture was refluxed for 5 hours. Thereafter, the reaction mixture was treated with hydrochloric acid and extracted with ethyl acetate to give, after concentration and filtration, 2-carboxy-5-methyl-pyrazine-4-oxide (3.5 g).

Melting point: 178°–180° C.

What is claimed is:

1. A process for the preparation of a pyrazine of formula I:

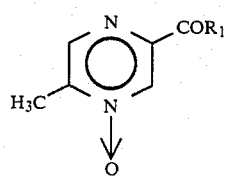

wherein R$_1$ is C$_1$–C$_6$ alkoxy, comprising:
(a) reacting a compound of formula II

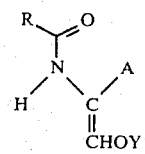

wherein R is selected from the group consisting of H, C$_1$–C$_6$ alkyl, and C$_1$–C$_6$ alkoxy; Y is selected from the group consisting of sodium ion, lithium ion and potassium ion; and A is COR$_1$; wherein R$_1$ is as defined above; with pyruvic aldehyde oxime of formula III,

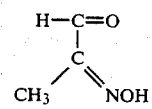

or a pyruvic aldehyde oxime acetal of formula IV

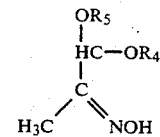

wherein R$_4$ and R$_5$ independent of one another, are H or C$_1$–C$_6$ alkyl; or R$_4$ and R$_5$ may form a cyclic acetal;

in the presence of an organic or inorganic acid selected from the group consisting of hydrochloric acid, hydrobromic acid, hydroiodic acid, sulfuric acid, nitric acid, p-toluene sulfonic acid, formic acid, phosphoric acid, methanesulphonic acid, trifluoroacetic acid, and trifluoromethanesulphonic acid;

in a solvent selected from the group consisting of water, R$_7$OH alcohols, R$_7$OR$_6$ ethers,

ketones, R$_7$CO$_2$R$_6$ esters or organic acids; wherein both R$_7$ and R$_6$, independent of one another, are a hydrogen atom, branched or linear C$_1$–C$_6$ alkyl or R$_6$ and R$_7$ together may form a cyclic C$_1$–C$_6$ alkyl, cyclic ether, cyclic ketone, or lactone;

at a temperature of from about 15° C. to about the boiling point of the solvent.

2. The process of claim 1 wherein R$_1$ in the compound of formula I is NH$_2$; said process further comprising:
(b) reacting the product of step (a) with gaseous ammonia.

3. The process of claim 1, wherein R$_1$ in the compound of formula I is hydroxyl; said process further comprising:
(c) hydrolyzing the product of step (a) with NaOH to obtain the compound of formula (I).

4. The process of claim 1, comprising reacting a compound of formula II and the acetal of formula IV, wherein the acetal is generated in situ by reacting hydroxylamine with a pyruvic aldehyde of the formula:

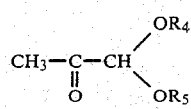
wherein $R_4$ and $R_5$ are as defined in claim 1.
5. The process of claim 1, wherein the acid is hydrochloric acid.
6. The process of claim 1, wherein the solvent is dioxane.
7. The process of claim 1, wherein the solvent is isopropyl alcohol.
8. The process of claim 1, wherein $R_1$ represents methoxy.
* * * * *